(12) United States Patent
Gallagher

(10) Patent No.: US 12,207,929 B2
(45) Date of Patent: Jan. 28, 2025

(54) SYSTEM AND METHOD FOR DEEP ANALYTICS AND STRATEGIC MONETIZATION OF BIOMEDICAL SENSOR DATA

(71) Applicant: Lear Corporation, Southfield, MI (US)

(72) Inventor: David Gallagher, Sterling Heights, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 18/427,257

(22) Filed: Jan. 30, 2024

(65) Prior Publication Data

US 2024/0164679 A1     May 23, 2024

Related U.S. Application Data

(63) Continuation of application No. 16/903,850, filed on Jun. 17, 2020, now Pat. No. 11,918,359.

(51) Int. Cl.
*A61B 5/18* (2006.01)
*A61B 3/11* (2006.01)
(Continued)

(52) U.S. Cl.
CPC ............... *A61B 5/18* (2013.01); *A61B 3/112* (2013.01); *A61B 3/113* (2013.01);
(Continued)

(58) Field of Classification Search
CPC ........... A61B 5/18; A61B 5/163; A61B 3/112; A61B 3/113; A61B 5/02055; A61B 5/4836; A61B 5/021; A61B 5/02438; A61B 5/0816; A61B 5/4266; G16H 40/67; G16H 50/70; G16H 50/20; G06V 40/193;
(Continued)

(56) References Cited

U.S. PATENT DOCUMENTS 9,389,595 B2 *   7/2016  Caskey ................... G06F 3/165
2008/0004950 A1 * 1/2008  Huang ............... G06Q 30/0271
                                                    705/14.66
(Continued)

OTHER PUBLICATIONS

Non-Final Office Action; related U.S. Appl. No. 16/903,850; date of mailing Jun. 24, 2022, 15 pgs.
(Continued)

*Primary Examiner* — Naomi J Small
(74) *Attorney, Agent, or Firm* — Brooks Kushman P.C.

(57) ABSTRACT

In at least one embodiment, a system for assessing biometric information for an occupant in a vehicle is provided. The system includes a plurality of sensors and a controller. The plurality of sensors is positioned about a main cabin of the vehicle and being configured to provide the biometric information for the occupant in response to a stimulus and to transmit a first signal indicative of the biometric information. The controller is positioned in the vehicle and is configured to activate the stimulus in the vehicle and to receive the biometric information after the stimulus has been activated. The controller is further configured to transmit the biometric information to at least one of another controller in the vehicle or to a server that is remote from the vehicle to assess the biometric information to determine the effect of the stimulus on the occupant.

20 Claims, 3 Drawing Sheets

(51) Int. Cl.

| | | |
|---|---|---|
| *A61B 3/113* | (2006.01) | |
| *A61B 5/00* | (2006.01) | |
| *A61B 5/0205* | (2006.01) | |
| *A61B 5/16* | (2006.01) | |
| *A61M 21/00* | (2006.01) | |
| *B60K 35/00* | (2006.01) | |
| *B60Q 9/00* | (2006.01) | |
| *G05B 19/042* | (2006.01) | |
| *G06F 3/16* | (2006.01) | |
| *G06V 40/18* | (2022.01) | |
| *G16H 40/67* | (2018.01) | |
| *G16H 50/20* | (2018.01) | |
| *G16H 50/70* | (2018.01) | |
| *A61B 5/021* | (2006.01) | |
| *A61B 5/024* | (2006.01) | |
| *A61B 5/08* | (2006.01) | |
| *G06Q 30/0201* | (2023.01) | |
| *G06Q 30/0242* | (2023.01) | |
| *G09F 21/04* | (2006.01) | |

(52) U.S. Cl.
CPC .......... *A61B 5/02055* (2013.01); *A61B 5/163* (2017.08); *A61B 5/4836* (2013.01); *A61M 21/00* (2013.01); *B60K 35/00* (2013.01); *B60Q 9/00* (2013.01); *G05B 19/042* (2013.01); *G06F 3/165* (2013.01); *G06V 40/193* (2022.01); *G16H 40/67* (2018.01); *G16H 50/20* (2018.01); *G16H 50/70* (2018.01); *A61B 5/021* (2013.01); *A61B 5/02438* (2013.01); *A61B 5/0816* (2013.01); *A61B 5/4266* (2013.01); *A61M 2021/0027* (2013.01); *A61M 2021/005* (2013.01); *G05B 2219/2637* (2013.01); *G06Q 30/0201* (2013.01); *G06Q 30/0242* (2013.01); *G09F 21/049* (2020.05)

(58) Field of Classification Search
CPC .......... A61M 21/00; A61M 2021/0027; A61M 2021/005; B60K 35/00; B60Q 9/00; G05B 19/042; G05B 2219/2637; G06F 3/165; G06F 21/049; G09F 21/049; G06Q 30/0201; G06Q 30/0242
USPC .......................................................... 701/36
See application file for complete search history.

(56) References Cited

U.S. PATENT DOCUMENTS

| | | | |
|---|---|---|---|
| 2015/0025917 A1* | 1/2015 | Stempora | G02B 27/0093 705/4 |
| 2015/0053066 A1* | 2/2015 | Hampiholi | B60K 35/10 84/602 |
| 2017/0337438 A1* | 11/2017 | El Kaliouby, Jr. | A61B 5/6893 |
| 2017/0351812 A1* | 12/2017 | Green | G16H 50/20 |
| 2018/0276362 A1* | 9/2018 | Baughman | G06F 21/32 |
| 2018/0349948 A1* | 12/2018 | Dow | G06Q 30/0244 |
| 2019/0108548 A1* | 4/2019 | Gaither | G06Q 30/0272 |
| 2019/0272755 A1* | 9/2019 | Giorgi | H04W 4/40 |
| 2019/0332902 A1* | 10/2019 | Gallagher | G06V 10/811 |
| 2020/0037945 A1* | 2/2020 | Yoon | B60W 60/0051 |
| 2020/0405213 A1* | 12/2020 | Chappell, III | A63F 13/79 |
| 2021/0284175 A1* | 9/2021 | Mehdi | B60K 35/65 |

OTHER PUBLICATIONS

Non-Final Office Action; related U.S. Appl. No. 16/903,850; date of mailing Dec. 30, 2022, 14 pgs.
Final Office Action; related U.S. Appl. No. 16/903,850; date of mailing Jul. 7, 2023, 6 pgs.

* cited by examiner

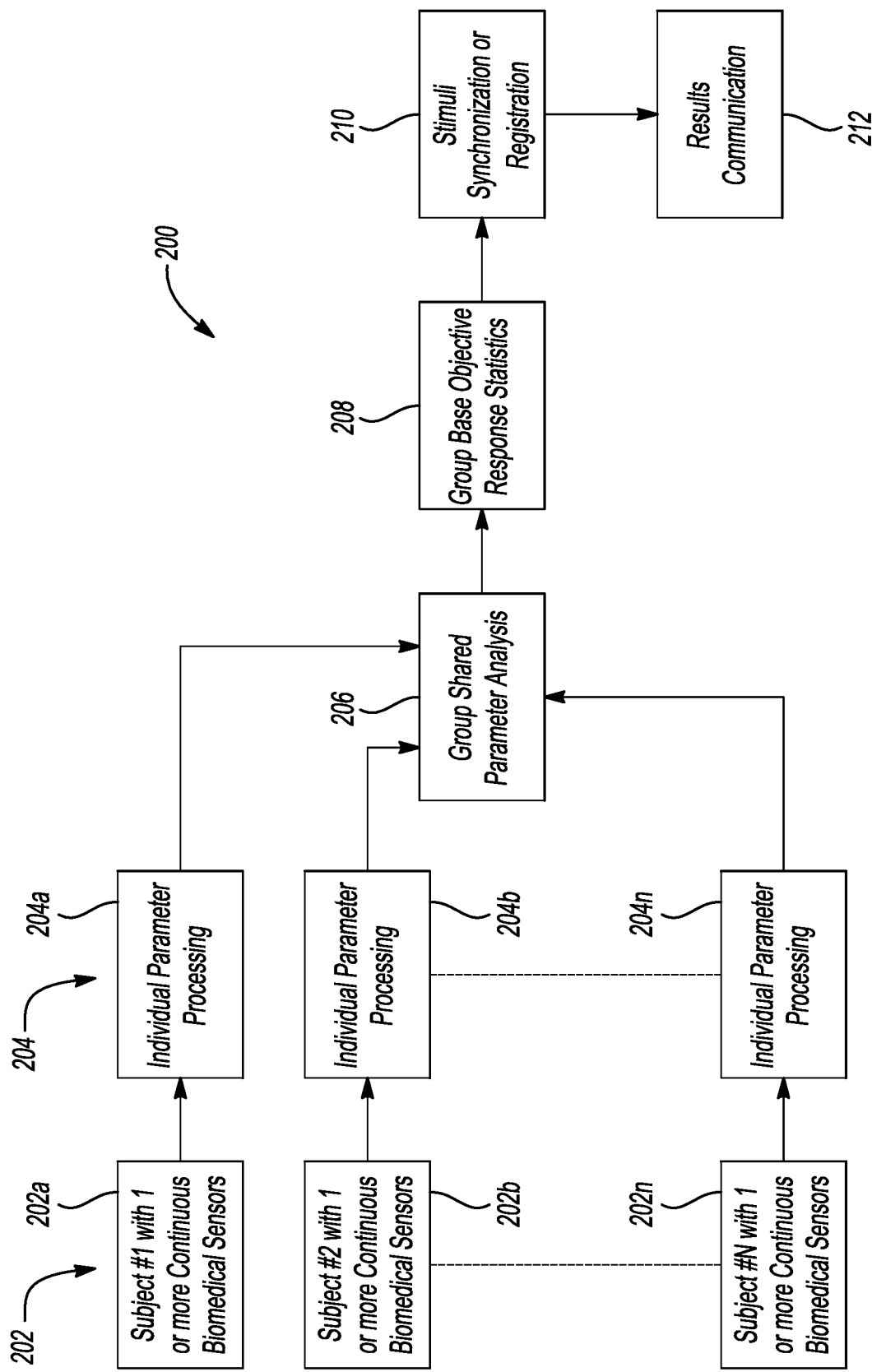

SYSTEM AND METHOD FOR DEEP ANALYTICS AND STRATEGIC MONETIZATION OF BIOMEDICAL SENSOR DATA

CROSS-REFERENCE TO RELATED APPLICATIONS

This application is a continuation of U.S. application Ser. No. 16/903,850 filed Jun. 17, 2020, now U.S. Pat. No. 11,918,359, issued Mar. 5, 2024, the disclosure of which is hereby incorporated in its entirety by reference herein.

TECHNICAL FIELD

Aspects disclosed herein may generally relate to a system and method for performing deep analytics and strategic monetization of biomedical sensor data. These aspects and others will be discussed in more detail below.

BACKGROUND

U.S. Publication No. 2018/0276362 to Baughman et al. provides a system and method for real world biometric analytics through the use of a multimodal analytic wallet. The system includes a biometric wallet comprising a pervasive repository for storing biometric data, the pervasive repository including at least one of a biometric layer, a genomic layer, a health layer, a privacy layer, and a processing layer. The biometric wallet further comprises a biometric analytic interface configured to communicate the biometric data to one or more devices.

U.S. Publication No. 2008/0004950 to Huang et al. ("Huang") provides an architecture for presenting advertisements in real-time in retail establishments. A sensor component includes sensors for collecting information about a customer or group of customers as they move through the store. The sensors can include capability for image processing, audio processing, light sensing, velocity sensing, direction sensing, proximity sensing, face recognition, pose recognition, transaction recognition, and biometric sensing, for example. A customer component analyzes the information and generates a profile about the customer. Advertisements are selected for presentation that target the customers as they walk in proximity of a presentation system of the store. An advertisement component facilitates dynamic presentation of a targeted advertisement to the individual as a function of the profile. The customer component can infer information during analysis using machine learning and reasoning.

SUMMARY

In at least one embodiment, a system for assessing biometric information for an occupant in a vehicle is provided. The system includes a plurality of sensors and a controller. The plurality of sensors is positioned about a main cabin of the vehicle and is configured to provide the biometric information for the occupant in response to a stimulus and to transmit a first signal indicative of the biometric information. The controller is positioned in the vehicle and is configured to activate the stimulus in the vehicle and to receive the biometric information after the stimulus has been activated. The controller is further configured to transmit the biometric information to at least one of another controller in the vehicle or to a server that is remote from the vehicle to assess the biometric information to determine the effect of the stimulus on the occupant.

In another embodiment, a system for assessing biometric information for an occupant in a vehicle is provided. The system includes a plurality of sensors and a controller. The plurality of sensors is configured to provide the biometric information for the occupant in response to a stimulus and to transmit a first signal indicative of the biometric information. The controller is positioned in the vehicle and is configured to receive the biometric information in response to a wearable device belonging to the occupant generating the stimulus for the occupant. The controller is further configured to wirelessly transmit the biometric information from the vehicle to a server that assesses the biometric information to determine the effect of the stimulus on the occupant.

In another embodiment, a system for assessing biometric information for an occupant is provided. The system includes a transceiver and a server. The server includes the transceiver and is configured to wirelessly receive biometric information from a plurality of vehicles for occupants in response to a stimulus occurring at each vehicle of the plurality of vehicles and to aggregate the biometric information to determine the effect of the stimulus for the occupant positioned in each of the plurality of vehicles.

BRIEF DESCRIPTION OF THE DRAWINGS

The embodiments of the present disclosure are pointed out with particularity in the appended claims. However, other features of the various embodiments will become more apparent and will be best understood by referring to the following detailed description in conjunction with the accompany drawings in which:

FIG. 2 depicts a method as executed by a server to perform deep analytics on received biometric information in accordance to one embodiment;

DETAILED DESCRIPTION

Figure 1:
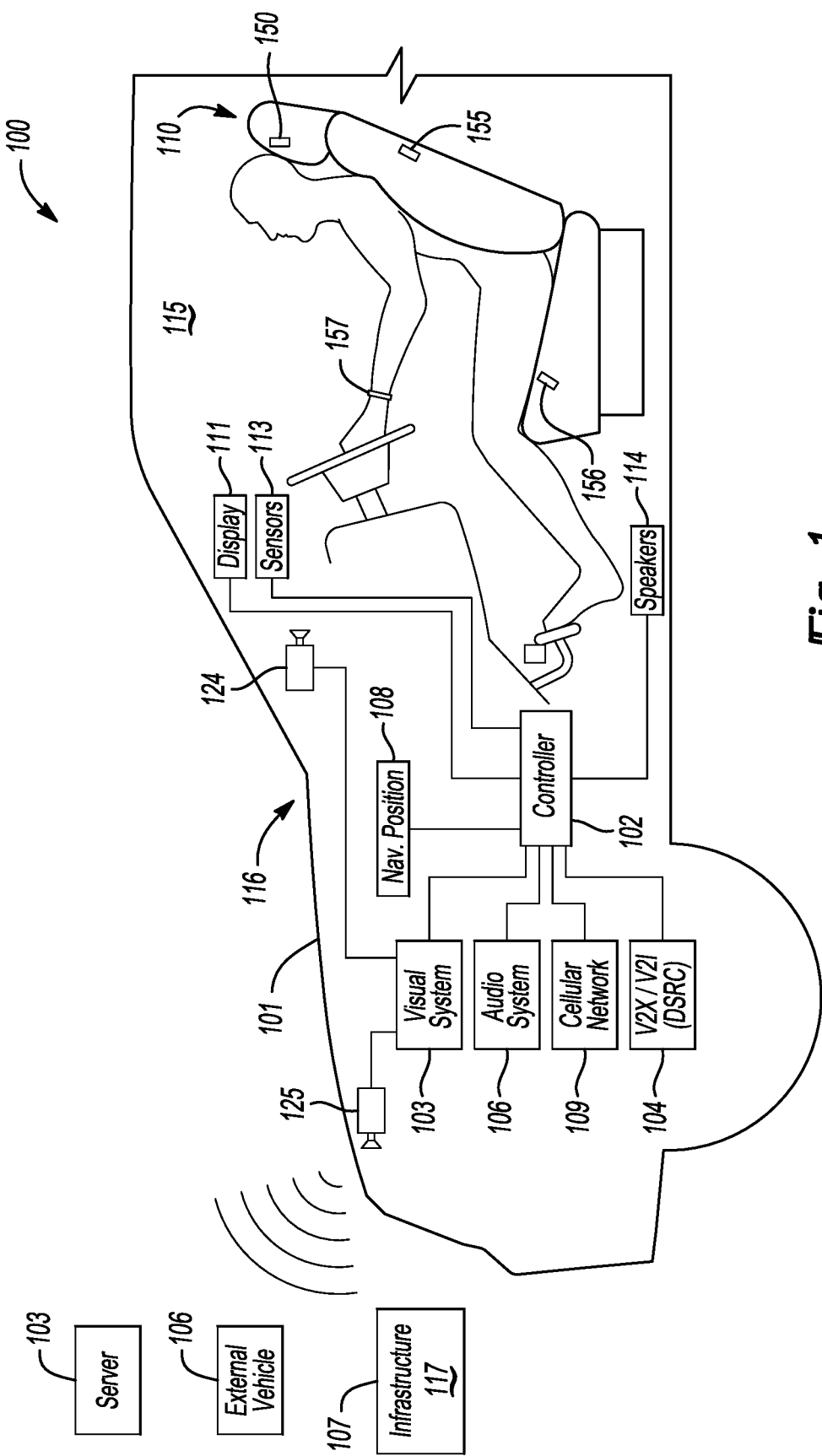
FIG. 1 depicts a system for performing deep analytics and strategic monetization of biomedical sensor data in accordance to one embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

It is recognized that the controllers as disclosed herein may include various microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, such controllers as disclosed utilizes one or more microprocessors to execute a computer-program that is embodied in a non-transitory computer readable medium that is programmed to perform any number of the functions as disclosed. Further, the controller(s) as provided herein includes a housing and the various number of microprocessors, integrated circuits, and memory devices ((e.g., FLASH, random access memory (RAM), read only memory (ROM), electrically programmable read only memory (EPROM), electrically erasable programmable read only memory (EEPROM)) positioned within the housing. The controller(s) as disclosed also include hardware-based inputs and outputs for receiving and transmitting data, respectively from and to other hardware-based devices as discussed herein.

An apparatus and method in which human biomedical sensor data monitoring of a subject's physiological and/or psychological states, conditions, and trends may be used to generate correlative information of high strategic and monetary value to a variety of consumers across many industries. A translational approach to taking biomedical information gathered from a subject by commercially available biomedical sensors (i.e. automotive biomedical devices, wearable devices such as watches, phones, and/or smart clothing, etc.) in or outside of the automotive environment that monitors physiological and/or psychological parameters such as automatic nervous system (ANS), central nervous system (CNS), somatic nervous system (SNS) activity and/or its combined activity and directly relates it to targeted surrounding/stimuli of that subject which is temporal and in designated cases, provides geographical precision and accuracy.

The disclosed system and method utilizes, among other things, this synchronization of sensed biomedical data of a subject, and then comparative analysis for group information (e.g. gender, age, etc.), to targeted external stimuli via, but not limited to, radio communications (e.g., advertisements/radio audio/personal music, etc.), geographical known visual references (e.g., billboard advertisements, store placements and signage, community areas, GPS tracked mobile stimuli), events (e.g., concerts), or pure geographical location (e.g., amusement parks, civil planning and engineering, real estate valuation) to assess that subject, particularly to the group based perception of that stimuli. While not exhaustive, one example monetization of this information includes continuous objective high-volume market analytics. This may correspond to non-specific analytics and a concern may be with the synchronization of the biomedical response of subjects, people, groups, etc. to known or knowable stimuli in "large numbers". In comparison to actual medical research, "large numbers" may be unheard of in typical biomedical studies. The aspects disclosed herein may utilize vehicle-to Vehicle-to-Everything (V2X), Vehicle-to-Infrastructure (V2I), or in non-automotive environments, Subject-to-Infrastructure (S2X) as well.

In biomedical research, where for instance the topic of research is human cognitive perception, emotion, mood, and/or behavioral characteristics group based biomedical data is gathered and analyzed to build a standard picture. By studying the group statistics of experimental results pertaining to such, the goal may be to paint a picture of normal or group dependent human function that is repeatable. In research, there are often contradictions and controversies that arise out of differing findings or lack or repeatability which can be confusing and troublesome. Interestingly enough, often these differences may not be conceptual flaws but methodological differences such as the selection of different paradigms, feature extraction methods, and/or stimuli specifics. This is well known to scientists and as such what is often created to combat this issue are paradigms or stimuli and stimuli packages that have been validated over large groups. For instance, one validated stimulus may be shown to produce an X+/Y quantitative response in metric Z for normal healthy subjects. One such example is the International Affective Picture System (IAPS), which is a an internationally applicable visual stimuli set of 944 images which have validated emotional ratings in terms of their valence, arousal, and dominance response.

Packages such as IAPS or the International Affective Digital Sounds (IADS) may be generated from hundreds and possibly thousands of subjects to focus in on which stimuli elicit the desired response(s) range for that packages intended use. If for example the same image to a large group of people is shown while monitoring their biomedical responses, it is possible to then build an objective statistical group response to that stimuli. This may be extended to monitoring a stimuli with a known response based on prior group data and correlating it to a specific subject or another group you are using the groups collective response to a known stimuli (e.g. radio advertisement on station X at 5:50 pm in this location with this number of applicable monitored subjects) to determine that the statistical response for a target group was objectively to that advertisement. In essence, it is the synchronization of the group-based response information to a shared stimulus for that group without requiring the group to interact or gather.

One example of the embodiment disclosed herein may ascertain if a radio advertisement is obtaining the proper attention for a particular target group at a specific time of day. For example, it may be possible to determine if drivers on the road are looking at a billboard and displaying the proper attention characteristics to billboard as they pass by. This is one of a number of examples as to the manner in which commercially available biomedical sensor technology may be employed to provide information to advertisers or to businesses in terms of monitoring the overall effectiveness of targeted advertisements to vehicle occupants. Such monitored data may be stored in a continuous objective nonspecific market analytics database. The use of one or more biomedical sensors can be employed to determine this information for an individual. From that group, information can then be determined. After which a variety of group breakdowns and categorizations may occur (age, gender, ethnicity, etc.). This data may be synchronized to stimuli that is shared among the group. For example, it may be possible to know what passengers passed a billboard, the radio station passengers were listening to and the time at which the passengers were listening, etc. This type of information may form highly valuable market data that provides measurable based precision that no subject market research firm may challenge. For example, the information collected via the embodiments disclosed herein may provide analytics-based revenue streams that may be exceptionally transformative and lucrative for a business entity that capitalizes on it.

The medical research community has demonstrated that through using only autonomic (ANS) bioinformation alone, for example, that complex mood and emotional state classification with high specificity can be achieved and in real time. Using such technology as heart and respiratory monitoring, eye tracking, and electrodermal response, information analyzed using standard linear feature extraction methods and complex chaotic nonlinear feature extraction methods that are highly precise and provide accurate classifications can be made about an occupants emotional and mood responses. Synchronization with group consumable stimuli to this data can provide information about the stimuli in addition to information about the subjects. This generally corresponds to the standard stimuli packages are selected and built. LAPS picture #X elicits that valence, arousal, dominance, value and range because the group study revealed that such aspects were the response to that stimuli. Data of physiological and/or physiological feature correlations connects the subjective to the objective such that bio-signal monitoring may allow for the same to be performed. Even with random uncontrolled stimuli, assuming a sample size is acquired for sufficient statistical power. The various aspects provided by the embodiments herein may be applicable to automotive and wearable devices. These aspects may not be able to be provided through traditional medical research and market research.

FIG. 1 depicts a system 100 for performing deep analytics and strategic monetization of biomedical sensor data in accordance to one embodiment. The system 100 generally includes a vehicle 101 and a server 103. In general, the vehicle 101 may monitor biometric information from any one or more vehicle occupants and wirelessly transmit such information to the server 103. The server 103 may aggregate such data and provide information to any one or more advertisers (or businesses) to assess the occupant's interest in products, services, etc. as offered by the advertisers through the vehicle 101.

The vehicle 101 includes a vehicle cabin 115 and an engine compartment 116. The vehicle 101 includes at least one controller 102 (hereafter "controller 102") having a microprocessor configured to execute any number of instructions for performing any of the disclosed operations as set forth herein. A first wireless interface processor 104 (e.g., a vehicle to vehicle (or V2X) processor with at least one transceiver or vehicle to infrastructure (or V2I)) 104 also with at least one transceiver) is provided in the vehicle 101 for enabling wireless transmission of, but not limited to, biometric information about one or more occupants in the vehicle 101 to the server 103. Alternatively, or additionally, the vehicle 101 may provide information to a vehicle external to the vehicle 101 (e.g., external vehicle 106) and/or to an infrastructure 107 via the first wireless interface processor 104. The infrastructure 107 may correspond to RFID readers, cameras, traffic lights, lane markers, streetlights, signage, parking meters, etc. Any one or more transmitters 117 (hereafter "transmitter") may be positioned on the foregoing devices that form the infrastructure 107.

It is recognized that the first wireless interface processor 104 may also receive information from the server 103, the external vehicle 106, and/or the infrastructure 107. For example, such information may correspond to stimulus information that is designed to elicit a reaction (e.g., positive or negative) for one or more occupants in the vehicle 101. The vehicle 101 is configured to capture biometric information that is indicative of the vehicle occupant's reaction and transmit the same to the server 103, the external vehicle 106, and/or the infrastructure 107. The stimulus information will be discussed in more detailed below.

Additionally, or alternatively, a second wireless interface processor 109 (e.g., cellular communications-based processor) may be used to establish bi-directional communication between the server 103, the external vehicle 106, and/or the infrastructure 107 with the vehicle 101. The second wireless interface processor 109 may also enable WiFi connectivity in accordance to IEE802.11 and Long-Term Evolution (LTE) connectivity with the controller 102 and/or a wearable device 157 belonging to any one or more of the occupants in the vehicle 101. Similarly, as noted above, the second wireless interface processor 109 may receive information from the server 103, the external vehicle 106, and/or the infrastructure 107. For example, such information may correspond to stimulus information that is designed to elicit a reaction (e.g., positive or negative) for one or more occupants in the vehicle 101. The vehicle 101 is configured to capture biometric information that is indicative of the vehicle occupant's reaction and transmit the same to the server 103, the external vehicle 106, and/or the infrastructure 107 via the second wireless interface processor 109.

The vehicle 101 further includes a navigational position system 108. The navigational position system 108 detects the position of the vehicle 101 by receipt of satellite signals or ground based position signals. The navigational position system 108 can include a global navigation satellite system (GNSS) such as Global Positioning System (GPS), Beidou, COMPASS, Galileo, GLONASS, Indian Regional Navigational Satellite System (IRNSS), or Quasi-Zenith Satellite System (QZSS). The navigational position system 108 may include a receiver that receives differential correction signals in North American from the FAA's WAAS system. The navigational position system 108 provides accurate position of the vehicle to the controller 102.

A vehicle seat 110 is positioned in the cabin 115 and is configured to support a driver or a passenger. The seat 110 includes a plurality of sensors 150, 155, 156 to detect various biometric characteristics of the person. The sensors 150 may be contactless and may be positioned on a headrest of the seat 110 to sense biometric information that corresponds to brain activity for the occupant in the seat 110. For example, the sensors 150 may detect or measure any one or more of an electroencephalogram (EEG), brain wave monitoring, etc. EEG corresponds to a test that is used to evaluate the electrical activity in the brain as brain cells communicate with each other through electrical impulses.

The sensors 155 and 156 may detect other biometric information. For example, the sensors 155, 156 may sense the heart rate of the occupant of the seat 110 and/or the breath rate of the occupant of the seat 110. For example, any one or more of the sensors 155 and 156 may employ Electromyography (EMG), ballistocardiography (BCG), siesmocardiography (SCG), photoplethysmography (PPG), respiration monitoring (RSP), an Electro-Dermal Response (EDR), Skin Conductance Response (SCR), blood pressure, and temperature. which generally corresponds to an indirect measure of sympathetic autonomic activity that is associated with both emotion and attention. In one example, the sensors 155 and 156 may be radar based for siesmocardiography and respiration monitoring.

EMG corresponds to a diagnostic procedure to assess the health of muscles and the nerve cells that control them (motor neurons). SCG corresponds to the recording of body vibrations induced by the heartbeat (e.g., SCG includes information on cardiac mechanics such as particular heart sounds and cardiac output). EDR corresponds to a measure of neurally mediated effects on sweat gland permeability such as observed as changes in the resistance of the skin to a small electrical current, or as differences in the electrical potential between different parts of the skin. SCR generally corresponds to an indirect measure of sympathetic autonomic activity that is associated with both emotion and attention.

It is recognized that wearable devices 157 (hereafter "wearable device 157) as positioned on the occupant may provide similar information as that provided by the sensors 150 and/or 155. The wearable device 157 may correspond to watches, phones (e.g. cellular), or other electronic monitoring devices or tags that may be coupled to clothing of the occupant. In these cases, non-vehicle-based communication may or may not be provided to communicate the biometric information to the server 103. For example, the wearable device 157 may simply use their own dedicated forms of wireless transmission to convey or transmit the biometric information to the server 103. The wearable device 157 may also generate the stimuli (e.g., advertisements that are generated from the mobile devices, tablets, etc.). This pertains primarily to non-driver occupants to avoid distractive behaviors in drivers. For these occupants the smart device usage information such as frequency of activity, browsing history, listening/engagement and the like can be fed to the vehicle 101 or to the smart phone (or the wearable device 157) through the vehicle 101 and to the server 103 to provide similar psychophysiological analysis and provide useful data to customers.

It is further recognized that the sensors 150, 155, 156 may also be positioned in the instrument panel, headliner of the vehicle 101, etc. The particular placement of the sensors 150, 155, 156 in the vehicle 111 may vary based on the desired criteria of a particular implementation.

A visual system 103 is provided to receive instructions from the controller 102 and produce visual displays in the vehicle, e.g., in the cabin on display screens 111 positioned on an instrument panel within the cabin 115. The displays produced by the visual systems 103 can be images sensed by an internal camera 124, an external camera 125, collision warnings, distraction warnings and the like. The visual system 103 can process the image data from the cameras 124, 125 before providing, the image data to the controller 102. The visual system 103 may process images to identify objects and the position of the driver in an example embodiment. Additional, the visual system 103 may capture the occupant's reaction to a stimulus and transmit an image of the occupant's reaction via the first wireless protocol controller 104 and/or the second wireless protocol controller 109 to the server 103, the external vehicle 106, and/or the infrastructure 107. Additionally, one or more eye gaze sensors 113 may be operably coupled to the controller 102 and capture biometric information corresponding to at least one of eye gaze, fixation time, gaze path, pupil dilation and area, etc. in response to the stimuli. The controller 102 may wirelessly transmit such information to the server 103, the external vehicle 106, and/or the infrastructure 107 for data aggregation and analysis in response to a predetermined stimulus corresponding to a predetermined advertisement that is presented to the occupant in the vehicle 101.

The vehicle 101 may also include an audio system 106 that may be part of a head unit. The audio system 106 may sense audio in the cabin 115 and output audio into the cabin, e.g., using multiple speakers 114. The controller 102 may be coupled to the audio system 106. In one example, the controller 102 may receive information from any or more of the server 103, the external vehicle 106, and/or the infrastructure 107 (e.g., via the first wireless interface processor 104 or the second wireless interface processor 109) to play audio corresponding to an audio advertisement at a particular time to the vehicle occupant positioned in the vehicle 101.

As noted above, the vehicle 101 may be programmed to provide stimulus (e.g., radio advertisement, visual display of advertisement on the display 111, etc.) and the occupant's response via their respective biometric information may be captured and transmitted from the vehicle 101. Likewise, the vehicle 101 may receive control signals from the transmitter 111 in the infrastructure 107 (e.g., building or any other object located street-side that is associated with a billboard) which control the one or more sensors 150, 155, 156 to capture the biometric information for the occupant in response to viewing the billboard from the vehicle 101.

The vehicle 101 transmits the captured biometric information to the server 103. It is recognized that the captured biometric information may also be transmitted to the external vehicle 106 and the infrastructure 107 which later transmits such information to the server 103 for analysis. The biometric information provides information pertaining to the overall effectiveness of the advertisement. For example, advertisers may be able to ascertain, but not limited to, whether a radio advertisement is catching the proper attention of a desired target group at that time of day and/or whether drivers on the road are looking at a billboard and displaying the proper attention characteristics to it as they pass by. These are but a few examples that the biometric information from the vehicle 101 can provide. The biometric information may be stored in a database associated with the server 103 and such data may be used to provide continuous objective nonspecific market analytics.

The server 103 may be generally configured to store samplings of biometric information form a large number of vehicle occupants from any number of vehicles and generate group information. After which, the server 103 may provide a variety of group breakdowns and categorization can occur (e.g., age, gender, ethnicity, etc.). This data may be synchronized to that stimuli that is shared among the group. Who passed that billboard, what station were they listening to? At what time? All of this becomes available to provide highly valuable market data in numbers that may be difficult to compete with globally and with measurable and evidence-based precision. This data may provide analytics-based revenue streams that could be exceptionally transformative and lucrative for a company that capitalizes on it. The server 103 generally provides for big data analytics techniques to be employed to provide end customers easy access to results from the pairing of stimuli to sensed biometric information. For example, the server 103 may employ methods such as clustering and dimension reduction patterns to large sets of data in an unsupervised fashion. The server 103 may also enable supervised methods such as classification and regression to be used to discover targeted trends as well. An ability to filter the database in the server 103 by components such as age, gender, stimuli, locality (e.g. based on collected vehicle GPS coordinates), and the like allow for quick extraction of information for more advanced analytics.

The medical research community has demonstrated that through using autonomic nervous system (ANS) bioinformation alone, for example, that complex mood and emotional state classification with a high degree of specificity may be achieved and in real time. Using such technology such as but not limited to, heart and respiratory monitoring, eye tracking, and electrodermal response, information may be analyzed using, for example, standard linear feature extraction methods and complex chaotic non-linear feature extraction methods that provide highly precise and accurate classifications about an occupant's emotional and mood responses. Synchronization with group consumable stimuli to this data may provide an indication about the stimuli in addition to the subjects themselves. This may be how standard stimuli packages are selected and built. A standardized stimuli system presenting stimuli identification, #X elicits reactions in valence, arousal, and dominance that reveal both mean and standard deviation values and ranges respective to each dimension because the group study data revealed that these ranges was their measured responses to that stimuli. Data in medical research pertaining to physiological and/or physiological feature correlations often seeks to connect the subjective measures to the objective stimuli to understand human group behavior. Bio-signal monitoring also allows for the same to be done by connecting objective stimuli to subjective responses to understand individual behavior. This aspect may be the case even with random uncontrolled stimuli assuming a sample size is acquired for sufficient statistical power. Additionally, this aspect may also apply, for example, to automotive or wearable device/smart technology.

Consider the following example, with the following setting and conditions: It is 5:20 pm on Tuesday and a commercial meant to target women ages 23-35 is played on the "most popular" top 40 radio station in particular region. In this case, the commercial is played back via the audio system 106. In response, the controller 102, at that particular time, collects the biometric information from the occupants via the sensors 150, 155, 156. In that region, assume for example that there are 5,000 vehicles equipped with sensors 150, 155, 156 that provides an occupant ID, heart and respiration monitoring, EDR, brain wave monitoring, and eye tracking. Of these 5,000 vehicles 2,900 are driven by women and 1,350 by women in that age range (e.g., 23-35). Of those women, 23% or 310 are listening to that station at that moment.

In general, the biometric information as collected from the vehicles 101 (e.g., via heart respiration monitoring, EDR, brain wave monitoring, eye tracking in addition to occupant ID), 237 of the women via the monitoring of such biometric information based on ANS, Somatic Nervous System (SNS), and Central Nervous System (CNS) provide the desired response of the advertisers. ANS related measures such as heart rate, respiration rate, and heart rate variability have strong correlation to the level of physiological arousal often indicative of the balance between sympathetic and parasympathetic nervous system activity. CNS monitoring via brainwaves may reveal cognitive processing and stimuli evoked responses in brain activity in bands such as alpha and beta as well as balances the bands. SNS monitoring for voluntary movement may reveal a level of discomfort, stress response, and/or may be used to correlate with in-vehicle voluntary actions. This response specificity may be known based on prior medical knowledge that illustrates a correlative connection between HRV, CRS, cognitive attention, eye gaze, pupil dilation to physiological and psychological statuses. The occupants' response may be purely arousal based & valence which includes dominance, cognitive in nature, or growth further in complexity to greater specificity by use of a circumplex model of affects and beyond.

In general, the server 103 may analyze the subject specific bio-signal measures in relation to stimuli single subject responses along with key identifiers to generate group statistics This data may allow advertisers to gauge the overall effectiveness of their commercial (or advertisements) with an accuracy and precision they could not have had. The data may be real, objective, and unobtrusive and provides unbiased feedback that is valuable to advertisers.

Consider another example, with the following settings and conditions: It is 10:15 pm on a Saturday and a large concert is held for 20,000 fans that targets men and women ages 18-45 with a specific cultural and economic background in a local arena. In this case, 22% of the crowd is wearing watches which gather heart related activity. The example illustrates that the biometric information may be collected via the wearable device 157 and that the aspects disclosed herein are not intended to be limited to the vehicle 101. The activation arousal patterns via HRV of the crowd throughout the concert can be monitored, analyzed, and synchronized with the event to identify the strongest and weakest reaction points of that event. Using this data, the producers of the event are capable of developing a better and potentially more lucrative tour or concert in the future. It is recognized that this may also apply to movies, amusement parks or any other large gatherings.

It is further recognized that OEMs or other vehicle suppliers may use the biometric information to assess overall satisfaction with vehicle functionality. For example, a vehicle fleet may be equipped with standard massage components and preprogrammed massage sequences for the seat 110. The server 103 may directly pair the received biometric information of the occupants with metrics such as time of use, frequency of use, manual adjustments, and efficacy of the profile. This data may be fed back to manufactures to improve existing features with over the air (OTA) updates, introduce new features with OTA updates, and/or design new standard features for the next generation of vehicles. Targeted patterns may be deployed to specific users in addition to individual specifics such as age, gender, and the like be made known for greater learning and segmentation. Another example may involve similar aspects but with heating and cooling features such as heating, cooling, and air conditioning (HVAC), seat 110, and/or main cabin 115 components such as the steering wheel.

FIG. 2 depicts a method 200 as executed by the server 103 to perform deep analytics on the biometric information in accordance to one embodiment.

In operation 202, the server 103 receives biometric information from a plurality of subjects (or occupants) 202a-202n from a plurality of vehicles 101 via the first wireless interface processor 104, the second wireless interface processor 109 or directly from the wearable device 157.

In operation 204, the server 103 processes, on an individual basis, each of the biometric information received from the plurality of subjects 202a-202n. The server 103 classifies individual occupant patterns and quantifies the same along with their key user identifiers and the stimulus information.

In operation 206, the server 103 performs grouped shared parameter analysis on the output of operation 204. The server 103 provides group patterns related to a stimuli are classified by aggregating the single occupant measures in operation 204 to find group based response information. The group-based response information may be segmented by key user identifier classes such as age, sex, location, income, etc. The server 103 synchronizes the stimulus in this operation to define a group based on shared stimulus.

In operation 208, the server 103 performs group based objective response statistics. The server 103 segment group-based patterns by measured response patterns, stimuli identifiers, and by key user identifier classes such as age, sex, location, and/or income level to provide queueable results as they related to target groups and stimuli reactions.

In operation 210, the server 103 associates or synchronizes the stimuli to the biometric information. For example, the server 103 associates the biometric information with the stimuli (e.g., radio advertisement, billboard advertisement, or advertisement offered through wearable devices 157). The server 103 associates or synchronizes the stimuli to the biometric information at an individual level and at a group level.

In operation 212, the server 103 transmits or provides the results from operation 210 to the advertiser. Alternatively, the server 103 may store such information and enable access to an advertiser. The server 103 itself may be under the control of a service provider and provide the associated biometric information along with the stimuli to advertisers.

Figure 3:
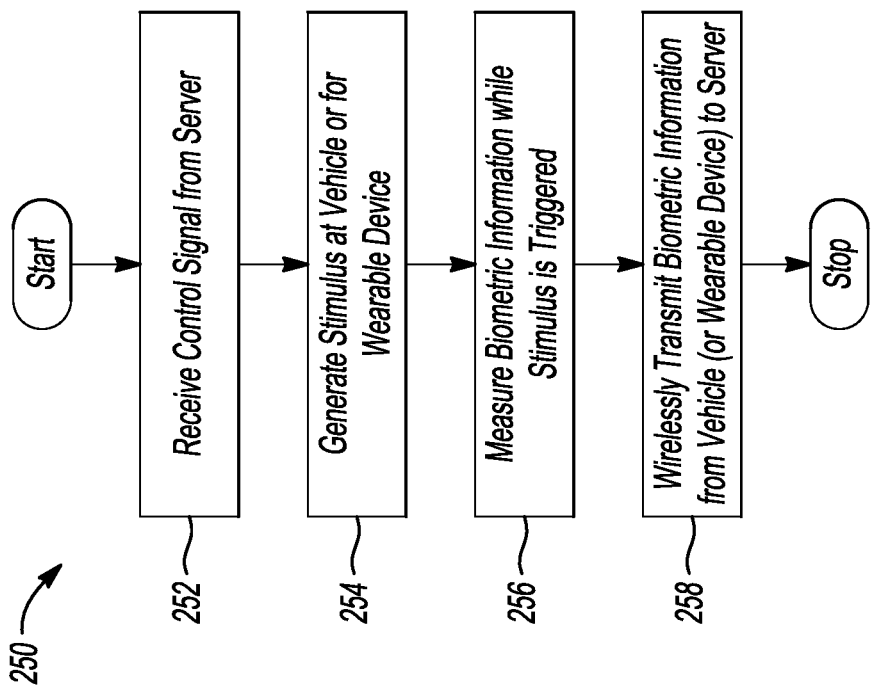
FIG. 3 depicts a method for generating a stimulus in the vehicle and for measuring biometric information in response to the stimulus in accordance to one embodiment.

FIG. 3 depicts a method 250 for generating a stimulus in the vehicle and for measuring biometric information in response to the stimulus in accordance to one embodiment. In operation 252, the controller 102 wirelessly receives a control signal from the server (e.g., via the first wireless interface processor 104 or the second wireless interface processor 109). The control signal is indicative of a predetermined time to receive and/or monitor measured biometric information from the sensors 150, 155, 156 in vehicle while the stimulus occurs. It is also recognized that the wearable device 157 (e.g., watch, tablet, mobile device, etc.) may also receive the control signal from the server 103.

In operation 254, the vehicle 101 generates the stimulus or alternatively the wearable device 157 generates the stimulus. As noted above, consider the example where it is desirable to monitor biometric information for an occupant in response to listening to a particular radio station at a predetermined time. The control signal may correspond to the time in which the radio station transmits the audio to trigger the stimulus for the occupant. The control signal serves as a trigger for the controller 102 to then store the measured biometric information (see operation 256) as received from the sensors 150, 155, 156 during or shortly after the predetermined time has elapsed and while the stimulus is activated. In response to receiving the measured biometric information, the controller 102 wirelessly transmits biometric information to the server 103 along with an indicator as to the stimulus (e.g., stimulus indicator) used to generate the biometric information (see operation 258).

This similarly applies to the wearable device 157 particularly if the wearable device 157 includes sensors that measures the biometric information for the occupant. For example, the vehicle 101 may transmit the advertisement via the audio system 106 and the control signal provides a predetermined time to the wearable device 157 such that the wearable device 157 measures the biometric information during the predetermined time or shortly after the predetermined time has elapsed (see operation 256). In response to receiving the measured biometric information, the controller 102 wirelessly transmits the biometric information to the server 103 along with the indicator as to the stimulus used to generate the biometric information (see operation 258).

Figure 4:
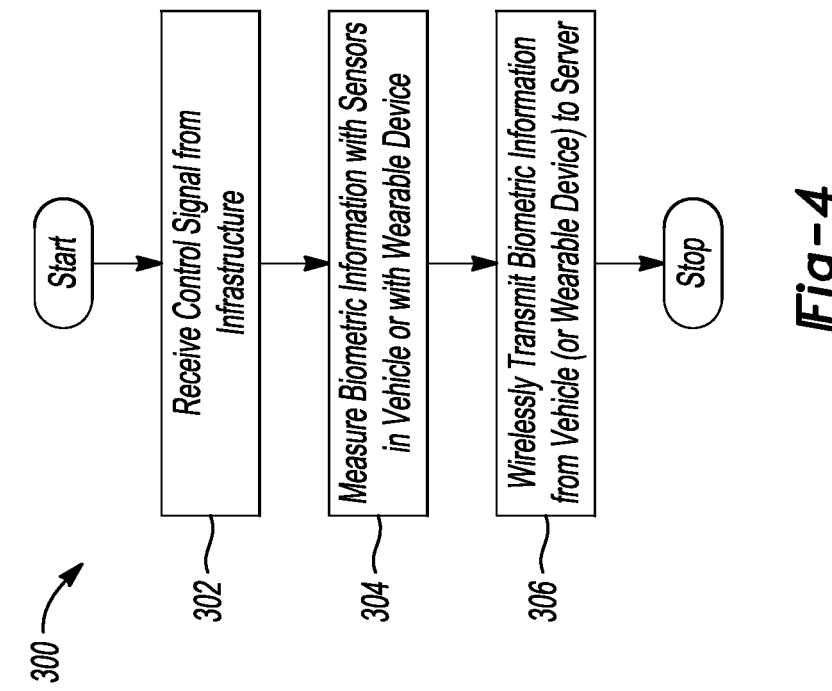
FIG. 4 depicts a method for measuring biometric information in response to a control signal from an transmitter located in an infrastructure in accordance to one embodiment.

FIG. 4 depicts a method 300 for generating a stimulus in the vehicle 101 and for measuring biometric information with the wearable device 157 in response to the stimulus in accordance to one embodiment.

In operation 302, the controller 102 and/or wearable device 157 wirelessly receives a control signal from the transmitter 117 associated with the infrastructure 107 (e.g., via the first wireless interface processor 104 or second wireless interface processor 109). The control signal is indicative of a predetermined time to receive and/or monitor measured biometric information from the sensors 150, 155, 156 in vehicle 101 (or from sensors already positioned on the wearable device 157) while the stimulus occurs such that the wearable device 157 (e.g., via the stimulus indicator associates and records the biometric information at the point in time in which the stimulus occurs (see operation 304). In this case, the stimulus may not be provided by the vehicle 101 and may correspond to a billboard positioned somewhere in the infrastructure 107 and it is desirable for advertisers of the billboard to assess the biometric information for occupants in the vehicle 101 to determine the level of impression made by the billboard on the occupant. In operation 306, the vehicle 101 and/or the wearable device 153 transmits the measured biometric information along with the stimulus indicator for the occupant(s) to the server 103.

While it is recognized the controller 102 and/or or wearable device 157 may wirelessly transmit the biometric information from the vehicle 101 to a server 103 to assess the biometric information to determine the effect of the stimulus on the occupant, the controller 102 and/or wearable device 157 may also perform the operations performed by the server 103 to assess the biometric information to determine the effect of the stimulus on the occupant. Alternatively, the controller 102 and/or wearable device 157 may also transmit the biometric information to another controller in the vehicle 101 to assess the biometric information and to determine the effect of the stimulus on the occupant in response to the biometric information.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system, comprising:
a processor configured to:
receive biometric information from a plurality of sensors deployed on-board a vehicle and wearable sensors associated with an occupant;
analyze data comprising the biometric information of the occupant and at least one of: a time of use, a frequency of use, manual adjustments, and an efficacy of use, associated with a plurality of features of the vehicle;
determine, based on the analysis, over the air (OTA) one or more updates related to the plurality of features in the vehicle; and
modify at least one of features of the vehicle based on the determined one or more OTA updates,
wherein the plurality of features comprises a massage feature, a heating feature, a cooling feature, and an air conditioning feature corresponding to a heating, ventilation, and air conditioning (HVAC) system deployed onboard the vehicle.

2. The system of claim 1, wherein the OTA updates are provided by at least one of an equipment manufacturer and a vehicle supplier.

3. The system of claim 1, wherein the processor is further configured to:
modify at least one of the plurality of features, the modification updating heating and cooling of a seat of the vehicle or main cabin components of the vehicle.

4. The system of claim 1, wherein the biometric information corresponds to at least one of a heart rate, a heart rate variability, a breath rate, a blood pressure, a temperature, a perspiration level, a brain activity, an eye tracking, and electro-dermal response (EDR).

5. The system of claim 4, the plurality of sensors comprising at least one of: an electroencephalogram (EEG) sensor configured to measure electroencephalogram information associated with a brain of the occupant, a brain wave monitoring sensor configured to monitor brain waves associated with the brain of the occupant, a heart rate sensor configured to monitor heart rate of the occupant, a siesmo-cardiography (SCG) sensor configured to monitor recording of body vibrations induced by the heartbeat, an Electro- Dermal Response (EDR) sensor configured to measure neurally mediated effects on sweat gland permeability, and a Skin Conductance Response (SCR) sensor configured to measure sympathetic autonomic activity.

6. The system of claim 5, wherein the processor is further configured to receive the biometric information from a plurality of contactless sensors deployed on-board the vehicle, wherein the contactless sensors are positioned on at least one of: an instrument panel of the vehicle, a steering wheel of the vehicle, a headrest of the vehicle, a seat back support of the vehicle, a seat bottom of the vehicle, and a headliner of the vehicle.

7. The system of claim 1, wherein the processor is further configured to modify a pre-programmed massage sequence of operations of a massage system of the vehicle executing the massage feature.

8. The system of claim 1, wherein the processor is further configured to receive biometric information from a plurality of vehicles associated with each of a plurality of occupants.

9. The system of claim 8, wherein the processor is further configured to receive the biometric information from the plurality of vehicles in response to a stimulus, the stimulus comprising at least one of a radio advertisement, a billboard and a video advertisement; and based on the biometric information from the plurality of vehicles, provide an output indicative of effectiveness of the stimulus in obtaining desired attention from the occupant.

10. The system of claim 9, wherein the processor is further configured to categorize the received biometric information based on an age, a gender, and an ethnicity of the plurality of occupants and synchronize the categorized information to the stimulus.

11. A method, comprising:
receiving biometric information from a plurality of sensors deployed on-board a vehicle and wearable sensors associated with an occupant;
analyzing data comprising the biometric information of the occupant and at least one of: a time of use, a frequency of use, manual adjustments, and an efficacy of use, associated with a plurality of features of the vehicle;
determining, based on the analysis, over the air (OTA) one or more updates related to the plurality of features in the vehicle; and
modifying at least one of features of the vehicle based on the determined one or more OTA updates, wherein the plurality of features comprises a massage feature, a heating feature, a cooling feature, an air conditioning feature corresponding to a heating, ventilation, and air conditioning (HVAC) system deployed onboard the vehicle.

12. The method of claim 11, wherein the OTA updates are provided by at least one of an equipment manufacturer and vehicle supplier.

13. The method of claim 11, further comprising modifying at least one of the plurality of features, the modification updating heating and cooling of a seat of the vehicle or main cabin components of the vehicle.

14. The method of claim 11, wherein the biometric information corresponds to at least one of a heart rate, a heart rate variability, a breath rate, a blood pressure, a temperature, a perspiration level, a brain activity, an eye tracking, and electro-dermal response (EDR).

15. The method of claim 14, the plurality of sensors comprising at least one of: an electroencephalogram (EEG) sensor configured to measure electroencephalogram information associated with a brain of the occupant, a brain wave monitoring sensor configured to monitor brain waves associated with the brain of the occupant, a heart rate sensor configured to monitor heart rate of the occupant, a siesmocardiography (SCG) sensor configured to monitor recording of body vibrations induced by the heartbeat, an Electro-Dermal Response (EDR) sensor configured to measure neurally mediated effects on sweat gland permeability, and an Skin Conductance Response (SCR) sensor configured to measure sympathetic autonomic activity.

16. The method of claim 15, further comprising receiving the biometric information from a plurality of contactless sensors deployed on-board the vehicle, wherein the contactless sensors are positioned on at least one of: an instrument panel of the vehicle, a steering wheel of the vehicle, a headrest of the vehicle, a seat back support of the vehicle, a seat bottom of the vehicle, and a headliner of the vehicle.

17. The method of claim 11, further comprising modifying a pre-programmed massage sequence of operations of a massage system of the vehicle executing the massage feature.

18. The method of claim 11, further comprising receiving biometric information from a plurality of vehicles associated with each of a plurality of occupants.

19. The method of claim 18, further comprising receiving the biometric information from the plurality of vehicles in response to a stimulus, the stimulus comprising at least one of a radio advertisement, a billboard and a video advertisement and based on the biometric information from the plurality of vehicles, provide an output indicative of effectiveness of the stimulus in obtaining a desired attention from the occupant.

20. The method of claim 19, further comprising categorizing the received biometric information based on an age, a gender and an ethnicity of the plurality of occupants and synchronizing the categorized information to the stimulus.

* * * * *